United States Patent [19]

Barcay et al.

[11] Patent Number: 5,464,613
[45] Date of Patent: Nov. 7, 1995

[54] FAT-BASED PEST BAIT

[75] Inventors: Stephen J. Barcay, Burnsville; Douglas G. Anderson, Lakeville, both of Minn.

[73] Assignee: Ecolab, Inc., St. Paul, Minn.

[21] Appl. No.: 261,461

[22] Filed: Jun. 17, 1994

[51] Int. Cl.$^6$ .......................... A01N 25/00; A01N 57/12; A01N 57/16; A01N 59/14
[52] U.S. Cl. .................. 424/84; 424/659; 514/89; 514/118; 514/547; 514/772; 514/785; 514/786
[58] Field of Search .................. 424/84, 659; 514/89, 514/118, 547, 772, 785, 786, 23, 53, 54, 64; 43/121, 132.1; 426/1

[56] References Cited

U.S. PATENT DOCUMENTS

| | | | |
|---|---|---|---|
| 3,716,600 | 2/1973 | Magee | 558/178 |
| 3,845,172 | 10/1974 | Magee | 558/178 |
| 3,887,710 | 6/1975 | Shaver et al. | 424/300 |
| 4,049,460 | 9/1977 | Broadbent | 424/84 |
| 4,388,297 | 6/1983 | Naffziger | 514/89 |
| 4,696,822 | 9/1987 | Matsumura et al. | 424/490 |
| 4,823,506 | 4/1989 | Demarest et al. | 43/131 |
| 4,841,669 | 6/1989 | Demarest et al. | 43/131 |
| 4,889,710 | 12/1989 | Hagarty | 424/45 |
| 4,959,221 | 9/1990 | Holmes | 424/659 |
| 4,988,511 | 1/1991 | Demetre | 424/84 |
| 4,988,516 | 1/1991 | Herring | 424/659 |
| 5,104,658 | 4/1992 | Hagarty | 424/405 |
| 5,116,618 | 5/1992 | Hagarty | 424/405 |
| 5,346,700 | 9/1994 | Stapleton et al. | 424/410 |
| 5,401,506 | 3/1995 | Chang et al. | 424/408 |

FOREIGN PATENT DOCUMENTS

| | | |
|---|---|---|
| 576034 | 6/1986 | Australia . |
| 0638237A1 | 8/1991 | European Pat. Off. . |
| WO91/07972 | 6/1991 | WIPO . |

OTHER PUBLICATIONS

Arthur G. Appel, *Laboratory and Field Performance of Consumer Bait Products for German Cockroach (Dictyopters: Blattellidae) Control*, Entomological Society of America 1990, pp. 153–159.

E. Paul Wileyto et al., *Attraction of the German Cockroach Blattella germanica (Orthoptera: Blatellidae), to Some Volatile Food Components*, Journal of Economic Entomology, vol. 76, No. 4, 1983, pp. 752–756.

Arthur G. Appel, *Performance of Gel and Paste Bait Products for German Cockroach (Dictyoptera: Blattellida) Control: Laboratory and Field Studies*, Entomological Society of America, vol. 85, No. 4, Aug. 1992, pp. 1176–1183.

Michael K. Rust, "Managing Household Pests", *Advances in Urban Pest Management*, G. W. Bennet and M. Owens (eds), Van Norstrand Reinhold, New York 1986, pp. 335–368.

William H. Robinson, *Proceedings of the National Conference on Urban Entomology*, 1992, pp. 77–91.

Michael K. Rust et al., *Attraction and Performance of Insecticidal Baits for German Cockroach Control*, International Pest Control 1981, pp. 106–109.

Hideakir Tsuji, *Attractive and Feeding Stimulative Effect of Some Fatty Acids and Related Compounds on Three Species of Cockroaches*, Japanese Journal of Sanitary Zoology 1966, pp. 89–96.

Kepner, R. L. et al., "Development of a Toxic Bait for Control of Mole Crickets (Orthoptera: Gryllotalpidae)," Journal of Economic Entomology, vol. 80(3), 1987, pp. 659–665.

*Primary Examiner*—Allen J. Robinson
*Assistant Examiner*—John D. Pak
*Attorney, Agent, or Firm*—Merchant, Gould, Smith, Edell, Welter & Schmidt

[57] ABSTRACT

Novel fat-based, substantially water-free, insecticidal compositions are described which are particularly effective against insect pests such as cockroaches, ants, termites, flies, etc. The compositions may be used in various forms depending on the targeted pests. As an example, the composition in the form of a paste can be applied into cracks and crevices for control of such pests and have the advantage of superior durability and prolonged attractiveness.

8 Claims, 3 Drawing Sheets

FAT-BASED PEST BAIT

FIELD OF THE INVENTION

This invention relates to a substantially water free fat-based pest bait for controlling insects, such as, for example, cockroaches, ants, termites, flies, etc.

BACKGROUND OF THE INVENTION

Historically, toxic baits for controlling crawling insects, such as cockroaches, have been water-based. With cockroaches especially, water is presumed necessary for good bait performance. Unfortunately, water-based bait products rapidly lose effectiveness due to water loss, rancidity, breakdown of active ingredients and other factors. Studies of water-based paste baits have confirmed that water loss, repellant properties of active ingredients, and insecticide resistance are the most important factors affecting bait performance, Appel, A. G. *J. Econ Entomol* 85 (4):1176–1183 (1992), Robinson, W. H. *Proceedings of the National Conference on Urban Entomology* 77–91 (1992), and Rust, N. K. "Managing Household Pests", in *Advances in Urban Pest Management*, G. W. Bennett and M. Owens (eds), Van Norstrand Reinhold, N.Y. 335–368 (1986).

The above problems have been solved by developing superior baits that are fat-based suspensions, designed to be applied, for example, as pastes to cracks and crevices for control of cockroaches, ants and other insects. These fat-based baits have the advantage of superior durability with prolonged attractiveness and stability of active and inert ingredients. Fat-based baits have the additional advantage of water repellency, allowing for durability in excessively damp environments.

SUMMARY OF THE INVENTION

Accordingly, the present invention is a substantially water-free insecticidal composition for use against insect pests consisting essentially of an effective amount of insecticide in admixture with a fat-based carrier.

A second aspect of the present invention is a substantially water-free insecticidal composition for use against insect pests comprising:

about 0.01–5.0 wt % acephate and about 95–99.99 wt % of a fat-based carrier.

A third aspect of the present invention is a substantially water-free insecticidal composition for use against insect pests comprising:

about 5–60 wt % boric acid and about 40–95 wt % of a fat-based carrier

Finally, the fourth aspect of the present invention is a method of controlling insect pests comprising applying to areas to be controlled a substantially water-free paste consisting essentially of an effective amount of insecticide and a fat-based carrier.

DETAILED DESCRIPTION OF THE INVENTION

Figure 1:
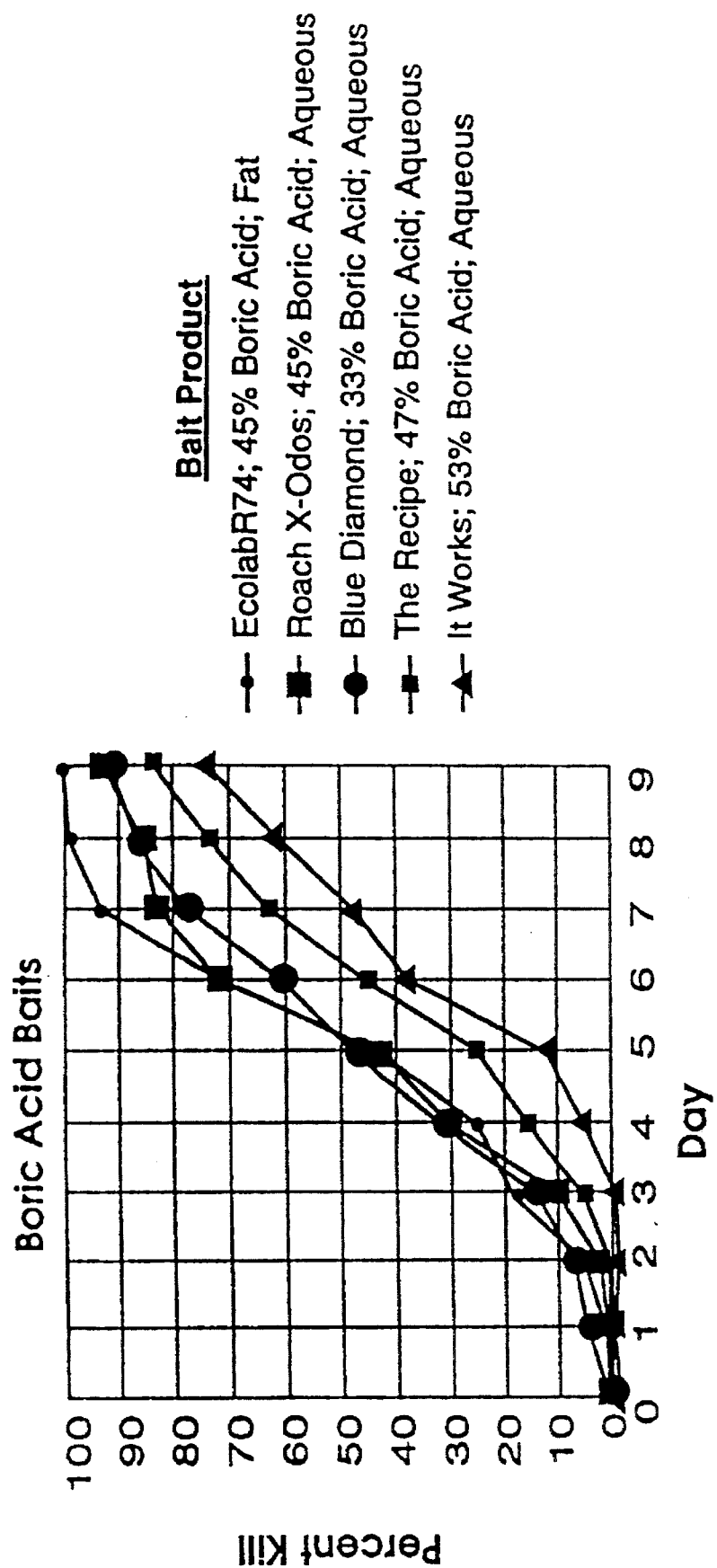
FIG. 1 is a plot of the mean cumulative percent kill of cockroaches as influenced by a fat-based boric acid bait product and fair water-based boric acid bait products (n=4, where n=number of replications). Exposure to these bait products is continuous and supplemented with alternative food and water.

The fat-based baits of the present invention are preferably used in the form of a paste and are substantially free of water. These fat-based baits may be modified by manufacturing to form a variety of different formulations and textures in addition to pastes, for example, granules, dusts, pellets, and the like. The use of the composition in containerized or non-containerized forms is designed against a wide variety of pests such as and including a wide variety of insects such as but not limited to, cockroaches, ants, crickets, termites, flies and the like.

Since the present invention is directed to the concept of a formulation which is essentially fat-based and substantially water-free, it can include in this composition any insecticide. Included as examples of active ingredients are compounds from the following classes of insecticides:

1—organophosphates, e.g. acephate, chlorpyrifos or diazinon;

2—mineral acids, e.g. boric acid;

3—carbamates, e.g. propoxur, 2-(1,3-dioxolane-2-yl)-phenyl-N-methyl carbamate, or o-isopropoxy-phenylmethyl-carbamate;

4—pyrethroids, e.g. cyfluthrin;

5—amidinohydrazones, e.g. hydramethylnon;

6—avermectins, e.g. abamectin;

7—chlorinated hydrocarbons, e.g. lindane, and combinations of the above with known synergists, such as carbamates or pyrethroids, e.g. o-isopropoxy-phenylmethylcarbamate or 2-(1,3-dioxolane-2-yl)- phenyl-N-methylcarbamate may be combined with piperonyl butoxide or piperonal bis-(2,2-butoxyethoxy)-ethyl acetal.

The term "fat-based" as employed throughout this application, including the claims, refers to the fact that a major portion of the composition contains fats present as glycerides and falling within a definition of fats as being "A glycerol ester of fatty acid(s): Fats generally are substances of plant and animal origin. Fat may be in a solid form, as tallow, lard, butter, margarine or other shortenings or in liquid form, e.g., as vegetable oils." Certain vegetable oils can also be solid depending on the degree of hydrogenation or saturation.

The glycerol esters are predominantly of the triglyceride type, vegetable oils and fats may also contain some di- and even mono-glycerides. Fatty acid component of fats and vegetable oils encompass the range of fatty acids containing from about 8–22 carbon atoms, primarily in a range of C12 and C18. Although most of the fatty acid content is saturated linear alkanoic acid, some of the fatty acid content may be unsaturated, as exemplified by oleic and linoleic acid. Examples of preferred fats and oils used in the present invention are partially hydrogenated vegetable oil comprising soy bean and cottonseed oil mixtures in solid or liquid flake form, partially hydrogenated cottonseed oil in solid form, partially hydrogenated soybean oil in solid form, partially hydrogenated vegetable oil containing a mixture of palm kernel and coconut oils in liquid form, partially hydrogenated nonvegetable coconut oil in liquid plastic form, partially hydrogenated vegetable oil in liquid flake form comprising a mixture of a palm kernel and cottonseed with lecithin, hydrogenated cottonseed oil, hydrogenated palm oil, hydrogenated soybean oil, hydrogenated vegetable oil in liquid form containing a mixture of rapeseed, cottonseed and soybean oil, partially hydrogenated vegetable oil containing a mixture of soybean and palm oil with vegetable mono and diglycerides and Tween 60K, in plastic form, partially hydrogenated vegetable oil containing soybean, cottonseed with vegetable mono and diglycerides in plastic form, partially hydrogenated vegetable oil in paste or margarine type of form which contains a mixture of soybean and cottonseed oils with water, salt, nonfat milk, lecithin, mono and diglycerides, sodium benzoate, artificial color, artificial flavor, vitamin A palmitate, soybean oil, corn oil, coconut oil, mono and diglycerides, ethoxylated mono and diglycerides, polyglycerol esters of fatty acids, and polyglycerol as fatty acids.

The term "fat-based carrier" used throughout the specification and in the claims refers to the composition of the present invention without the active ingredient, the insecticide. The carrier is the diluent, excipient or matrix which contains, protects, supports or envelopes the insecticide. The "fat-based carrier" thus includes as the essential and major component the fats defined above but may also contain, if desired, preservatives, flowing agents, and the like. The "fat-based carrier" may also contain attractants and feeding stimulants depending on the targeted pest. Feeding stimulants are, for example, carbohydrates, carbohydrate complexes. Examples of carbohydrates are maltodextrins and the like; carbohydrate complexes, corn syrup solids, protein such as yeast extracts, milk solids, sugars such as sucrose, glucose, fructose, starches such as corn, potato and the like. Examples of attractants are odorants and flavorants such as, for example, cyclotenes and the like, plant extracts such as fenugreek and the like, alcohols such as ethanol, or a volatile ester in combination with ethanol. Said volatile ester is made from a combination of a $C_1$–$C_6$ branched or unbranched alcohol with a $C_1$–$C_3$ carboxylic acid. Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof, etc. Carboxylic acids useful in manufacturing the ester attractant of the invention include acetic acid, propionic acid, butyric acid, mixtures thereof, and others. The associated reactive analogs of the respective carboxylic acids can be used, for example, the acid chloride or acid anhydride. The preferred volatile ester for use is a lower alcohol acetate ester such as n-amyl acetate, isoamyl acetate, isobutyl acetate, n-propyl acetate, ethyl acetate or mixtures thereof. Some of the ingredients may overlap in category as they can be both attractants and feed stimulants, for example proteins mentioned above, odorants and flavorants.

While any insecticide can be used in the present invention including the classes of insecticides defined above, those particularly named among the classes constitute preferred embodiments. An effective amount of insecticide may vary depending on the choice of insecticide and the targeted pest. For example, for the classes of insecticides defined above, with the exception of boric acid, an effective amount of insecticides may be as low as about 0.001 wt % of the composition. Thus, a range of such insecticide to provide an effective amount may be from about 0.001 wt % to about 5.0 wt %. Acephate, chlorpyrifos and boric acid are more preferred, acephate being the most preferred. Acephate is a fine crystalline powder that is water soluble and can be incorporated easily into a fat forming a suspension or paste. Acephate is also desirable as an active ingredient since there is no known insecticide resistance and it has very low repellency and mammalian toxicity. Chlorpyrifos is also commercially available in microencapsulated form and this most preferred chlorpyrifos formulation can also be incorporated easily into a fat forming a suspension or paste. Such formulations are very fast acting and durable.

Thus, a preferred embodiment includes a substantially water-free insecticidal composition comprising about 0.01–5.0 wt % acephate or chlorpyrifos, and about 95–99.99 wt % of a fat-based carrier. A more preferred composition comprises about 0.1–5.0 wt % acephate or chlorpyrifos and about 95–99.9 wt % of a fat-based carrier.

Another preferred embodiment is a substantially water-free insecticidal composition comprising about 5–60 wt % boric acid, and about 40–95 wt % of a fat-based carrier.

As an example of a preferred insecticide fat-based bait formulation, other than boric acid, the following ingredients and ranges are representative:

about 0.1–5.0 wt % acephate or chlorpyrifos
about 5.0–50.0 wt % hydrogenated soybean oil
about 20.0–50.0 wt % soybean oil in liquid form
about 1.0–20.0 wt % sucrose
about 0.02–0.1 wt % BHT (preservative)
about 1.0–20.0 wt % corn syrup solids
about 1.0–20.0 wt % maltodextrins
about 1.0–20.0 wt % yeast extract
about 0.1–1.0 wt % fenugreek extract With exception to the active ingredient and the fats, the remaining ingredients cited above are optional components in the compositions. Any one or more of these ingredients can be but need not be present in the compositions.

As an example of a boric acid fat-based bait formulation, the following representative ranges are also preferred for the compositions:

about 5.0–60 wt % boric acid
about 5–50.0 wt % a hydrogenated soybean oil
about 20.0–50.0 wt % soybean oil
about 1.0–20.0 wt % sucrose
about 0.02–0.1 wt % BHT (preservative)
about 1.0–20.0 wt % yeast extract
about 0.1–1.0 wt % fenugreek extract With the exception of the fats and the boric acid active ingredient, one or all of the remaining ingredients can be present in the formulation but are optional only.

As a paste, the above described compositions can be used as containerized or non-containerized baits, the application depending on the targeted pest. As an example, paste formulations may be applied in cracks and crevices of apartments, homes or industrial settings where pests, especially cockroaches and ants are likely to reside. Pastes are applied into cracks and crevices, for example, in the kitchens and bathrooms of the above structures for effective control and killing of these pests. The pastes can be manufactured by well-known methods which essentially comprise blending the active insecticide into the fat-based carrier containing a mixture of solid and liquid fats. Additional ingredients, if desired, are also added during the blending operation.

The following examples are used to illustrate the present invention but are not limiting thereon.

EXAMPLE 1

Bait Formulation Paste

The following ingredients are blended
- 1.0 wt % acephate
- 20.0 wt % sucrose
- 25.0 wt % saturated soybean oil
- 5.0 wt % yeast extract
- 15.75 wt % margarine or shortening
- 33.0 wt % soybean oil
- 0.15 wt % fenugreek extract
- 0.10 wt % butylated hydroxy toluene (BHT)

EXAMPLE 2

The following fat-based baits were formulated to optimize both palatability to cockroaches and durability of the bait. These baits were found superior to existing commercial water-based baits in terms of efficacy, FIG. 1 and durability, Table 1.

A. Boric Acid Fat-Based Formulation
The following ingredients were blended:
- 45.0 wt % boric acid
- 7.5 wt % sucrose
- 7.4 wt % corn syrup solids
- 28.0 wt % soybean oil
- 11.9 wt % entrapped water powder
- 0.1 wt % fenugreek extract
- 0.1 wt % BHT B. Acephate Fat-Based Formulations
Four formulations were prepared by blending 0.1, 0.25, 0.5 and 1.0 wt % acephate with:
- 35.0 wt % sucrose
- 29.7–28.8 wt % maltodextrins
- 35 wt % soy shortening
- 0.1 wt % fenugreek extract
- 0.1 wt % BHT C. Microencapsulated Chlorpyrifos Fat-Based Formulations Four formulations were prepared by mixing 0.1, 0.25, 0.5 and 1.0 wt % microencapsulated chlorpyrifos with:
- 25.0 wt % sucrose
- 45.0 wt % soy shortening
- 29.9–29.0 wt % wheat flour D. For comparative purposes, two commercially available water-based baits were used:
  (i) STAPLETONS MAGNETIC ROACH FOOD (MRF), Blue Diamond Exterminating & Manufacturing Co., which contains 33.3. wt % boric acid, and
  (ii) The Recipe, Earth Friendly Products, which contains 47.0 wt % boric acid.

METHODS FOR BAIT EVALUATIONS

Figure 2:
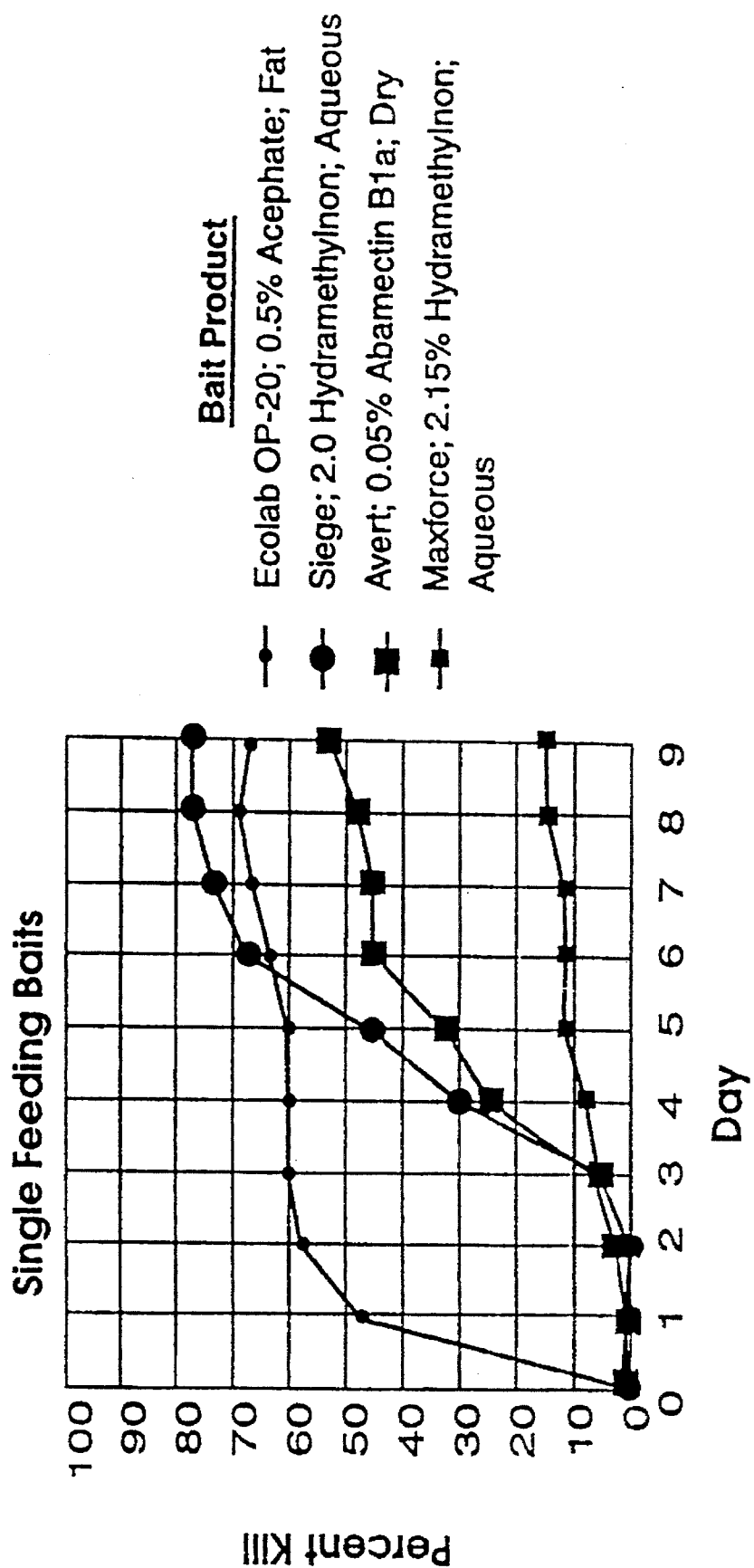
FIG. 2 is a plot of the mean cumulative percent kill of cockroaches as influenced by acephate fat-based bait product and two aqueous and one dry products (n=4). A single exposure to the bait was followed by recovery with food and water.
Figure 3:
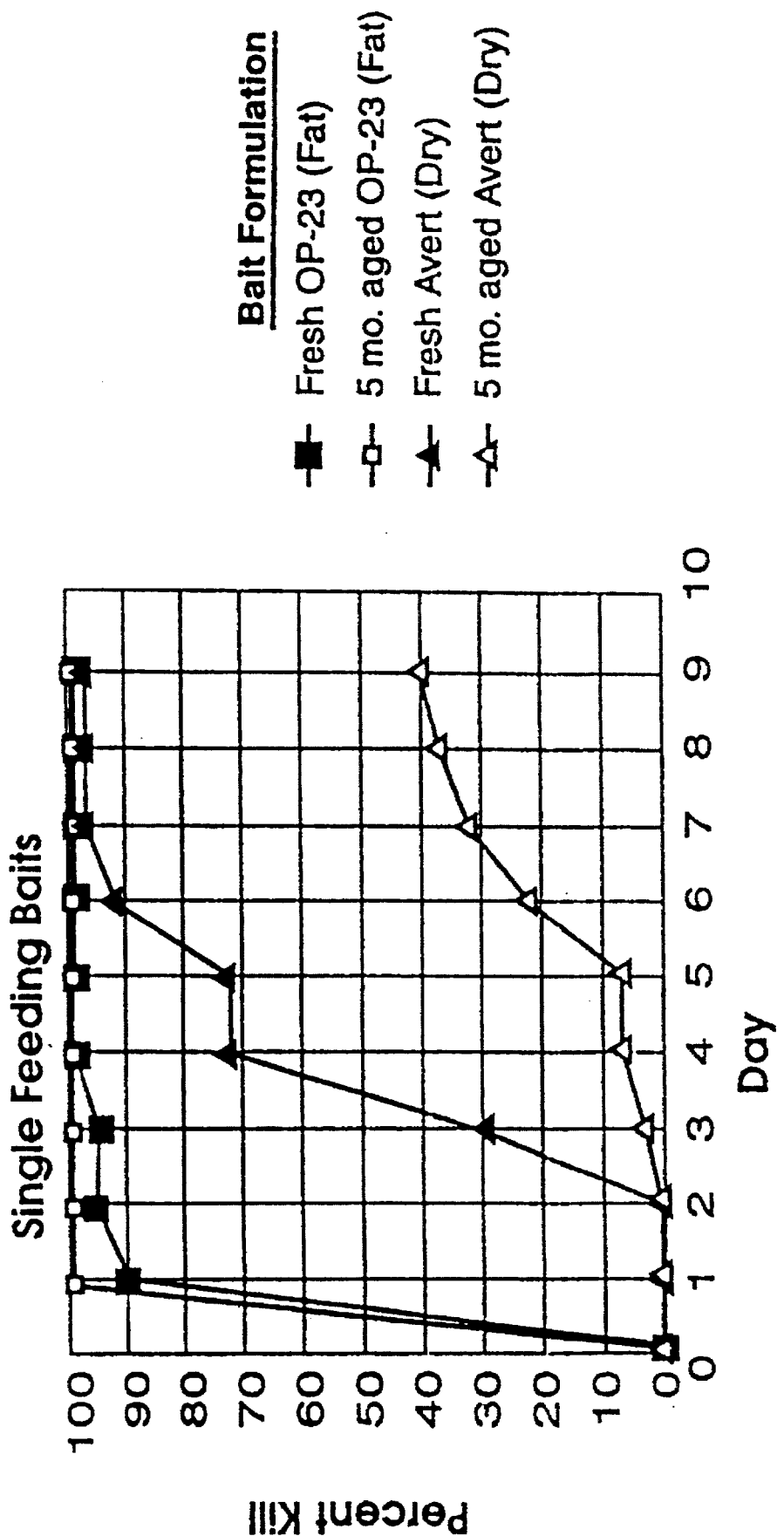
FIG. 3 is a plot of the mean cumulative percent kill of cockroaches from exposure to microencapsulated chlorpyrifos fat-based bait (n=4). A single exposure to the bait was followed by recovery with food and water.

Choice tests were performed against German cockroaches for the purpose of evaluating toxic bait efficacy as influenced by bait aging. German cockroach adult males were placed into jars and provided with food and water. The Jars were greased around the upper lip with petrolatum to prevent escape. After an acclimation period, cockroaches were presented with a bait. In these tests, cockroaches were allowed to choose between an alternative food source (Purina Dog Chow) and the bait. The boric acid baits tested were the commercially available materials described above and the formulation of Example 2A. Single feeding baits were also tested: the acephate formulation at 0.5% concentration described in Example 2B above and the microencapsulated chlorpyrifos formulation at 0.5% described in Example 2C above. Cockroaches were exposed to the boric acid base continuously. For the single feeding baits, a single exposure was followed by recovery with food and water. Baits were aged out to 5 months at 50% humidity and 80° F. Observations of bait attractiveness, palatability, and daily mortality after exposure to the bait were recorded. There were four replications in each treatment. As stated above, the results are shown in FIG. 1 and Table 1. Results on the efficacy of the acephate and microencapsulated chlorpyrifos formulations are shown in FIGS. 2 and 3, respectively.

TABLE 1

Efficacy of Baits as Influenced by Aging

| Formulation | Exposure Type | % Mortality 7 days after exposure for aging period: | |
|---|---|---|---|
| | | Fresh | 5 Months |
| Example 2A Fat Based | Continuous + Food & Water | 92.5 | 100.0 |
| Example 2B Fat Based | Single + Food & Water | 100.0 | 100.0 |
| The Recipe 47.0% Boric Acid Aqueous Based | Continuous + Food & Water | 62.5 | 33.33 |
| MRF 33.3% Boric Acid Aqueous Based | Continuous + Food & Water | 77.5 | 12.5 |

We claim:

1. A substantially water-free insecticidal composition for use against insect pests comprising:
   about 0.01–5.0 wt % acephate, and
   about 95–99.99 wt % of a fat-based carrier comprising a mixture of a solid fat and a liquid fat.

2. The composition of claim 1, wherein the fat-based carrier consists essentially of a mixture of hydrogenated soybean oil and soybean oil.

3. The composition of claim 1, wherein the fat-based carrier further contains an insect attractant.

4. The composition of claim 1, wherein the fat-based carrier further contains a feed stimulant.

5. The composition of claim 1 in the form of a paste.

6. A substantially water-free insecticidal composition for use against insect pests comprising:
   about 0.1–5.0 wt % acephate, and
   about 95–99.9 wt % of a fat-based carrier comprising a mixture of a solid fat and a liquid fat.

7. A method of controlling insect pests comprising applying to areas to be controlled an effective amount of a substantially water-free insecticide composition comprising: about 0.01–5.0 wt % acephate, and about 95–99.99 wt % of a fat-based carrier comprising a mixture of a solid fat and a liquid fat.

8. The method of claim 7, wherein the composition comprises:
   about 0.1–5.0 wt % acephate, and
   about 95–99.9 wt % of a fat-based carrier comprising a mixture of a solid fat and a liquid fat.

* * * * *

UNITED STATES PATENT AND TRADEMARK OFFICE
CERTIFICATE OF CORRECTION

PATENT NO. : 5,464,613

DATED : November 7, 1995

INVENTOR(S) : Barcay et al.

It is certified that error appears in the above-identified patent and that said Letters Patent is hereby corrected as shown below:

On column 1, line 62, please delete "fair" and substitute therefore --four--

On column 2, line 6, please insert --product (OP-23), fresh and 5 mo. aged, and a dry product, fresh and 5 mo. aged-- after the word "bait"

On column 5, line 50, please insert --TM-- after the word "FOOD"

On column 5, line 53, please delete "The Recipe" and substitute therefore --THE RECIPE™--

On column 6, line 27, please delete "The Recipe" and substitute therefore --THE RECIPE™--

Signed and Sealed this

Fifth Day of March, 1996

Attest:

BRUCE LEHMAN

Attesting Officer

Commissioner of Patents and Trademarks